United States Patent [19]
Chen

[11] Patent Number: 4,601,830
[45] Date of Patent: Jul. 22, 1986

[54] METHOD FOR DIALYSIS

[75] Inventor: Wei-Tzuoh Chen, Downers Grove, Ill.

[73] Assignee: The United States of America as represented by the Administrator of Veteran Affairs, Washington, D.C.

[21] Appl. No.: 315,668

[22] Filed: Oct. 28, 1981

Related U.S. Application Data

[63] Continuation of Ser. No. 95,468, Nov. 19, 1979, abandoned.

[51] Int. Cl.$^4$ .............................................. B01D 13/00
[52] U.S. Cl. .................................. 210/647; 210/96.2; 210/321.3
[58] Field of Search ...................... 210/96.2, 321.3, 647

[56] References Cited

U.S. PATENT DOCUMENTS 4,153,554  5/1979  von der Heide et al. ..... 210/96.2 X

FOREIGN PATENT DOCUMENTS 2825134  12/1978  Fed. Rep. of Germany ..... 210/96.2

OTHER PUBLICATIONS

Lai et al., "Third Generation Artificial Kidney: pH and Concentration Control", from vol. XXI, Trans. Amer. Soc. Artif. Int. Organs, 1975, pp. 346-352.

Zelman et al., "Augmentation of Peritoneal Dialysis Efficiency with Programmed Hyper/Hypoosmotic Dialysates", from vol. XXIII, Trans. Am. Soc. Artif. Intern. Organs, 1977, pp. 203-209.

*Primary Examiner*—Frank Spear
*Attorney, Agent, or Firm*—Wood, Dalton, Phillips, Mason & Rowe

[57] ABSTRACT

A method and apparatus for the hemodialysis of the blood of kidney failure patients. The concentration of the dialysis solution is initially selected so that the solution osmolality approximates the osmolality of the patient's blood. The dialysis solution concentration is then reduced linearly as a function of time as the dialysis is carried out. The conductivity of the dialysis solution is measured and compared with high and low limit references. If the conductivity is outside the limits, an alarm is given and the concentration of the dialysis solution is held constant. A timer controls a proportional pumping means to reduce the concentration of the dialysis solution and concurrently reduces the conductivity reference limits for the alarm.

6 Claims, 4 Drawing Figures

METHOD FOR DIALYSIS

This is a continuation of application Ser. No. 95,468 filed Nov. 19, 1979, now abandoned.

This invention relates to a method and apparatus for dialysis in which the concentration of the dialysis solution is varied as a function of time during the treatment.

BACKGROUND OF THE INVENTION

A patient undergoing dialysis often suffers uncomfortable and debilitating side effects as nausea, vomiting, headaches, hypotension and the like. It is theorized that these side effects are caused by the disequilibrium or substantial difference between the osmolality level of the patient's blood and that of the dialysis solution during the dialysis procedure. The flow of blood through the dialyzer is changed markedly by removing osmotic particles and other substances. This kind of treatment causes a disequilibrium in the patient's body system precipitating the side effects noted above.

SUMMARY OF THE INVENTION

In accordance with this invention, I provide a dialysis method and an apparatus for carrying out the method in which the dialysis solution concentration is initially established with an osmolality at a level comparable with the osmolality of the patient's blood. During the course of the dialysis treatment, the concentration of the dialysis solution is reduced at a rate corresponding generally with the reduction of osmolality of the blood, as impurities are removed. Thus, the disequilibrium in the patient's system is minimized.

Another feature of the invention is that the concentration of the dialysis solution to the dialyzer is reduced linearly as a function of time.

A further feature is that the conductivity of the dialysis solution is measured and compared with a reference or upper and lower conductivity limits. These limits are varied as a function of time to correspond with the reduction in dialysis solution concentration. If the conductivity of the dialysis solution departs from the reference, an alarm is given.

Yet another feature is that the linear reduction of dialysis solution concentration may be interrupted and the concentration held constant or adjusted by the operator.

BRIEF DESCRIPTION OF THE DRAWINGS

Further features and advantages of the invention will readily be apparent from the following specification and from the drawings, in which.

DETAILED DESCRIPTION

In a typical dialysis system, concentrated dialysis solution is mixed with product water (deionized water treated to remove trace metals). The water is preferably heated to blood temperature prior to mixing. The mixture is circulated through the dialyzer. The mixing of concentrated dialysis solution and heated product water may be performed by a proportioning pump, such as the piston pumps shown in Willock U.S. Pat. Nos. 3,406,826 and 3,598,727; or by motor driven positive displacement rotary pumps as shown in Frasier et al U.S. Pat. No 3,878,095. Commonly the ratio of concentrated dialysis solution to water is 1:34. This corresponds with an osmolality which is lower than that of a kidney failure patient's blood at the start of the dialysis procedure. This difference in osmolality contributes to a disequilibrium syndrome in the patient, reflected in a blood pressure change and other undesirable side effects noted above after hemodialysis treatment.

Figure 1:
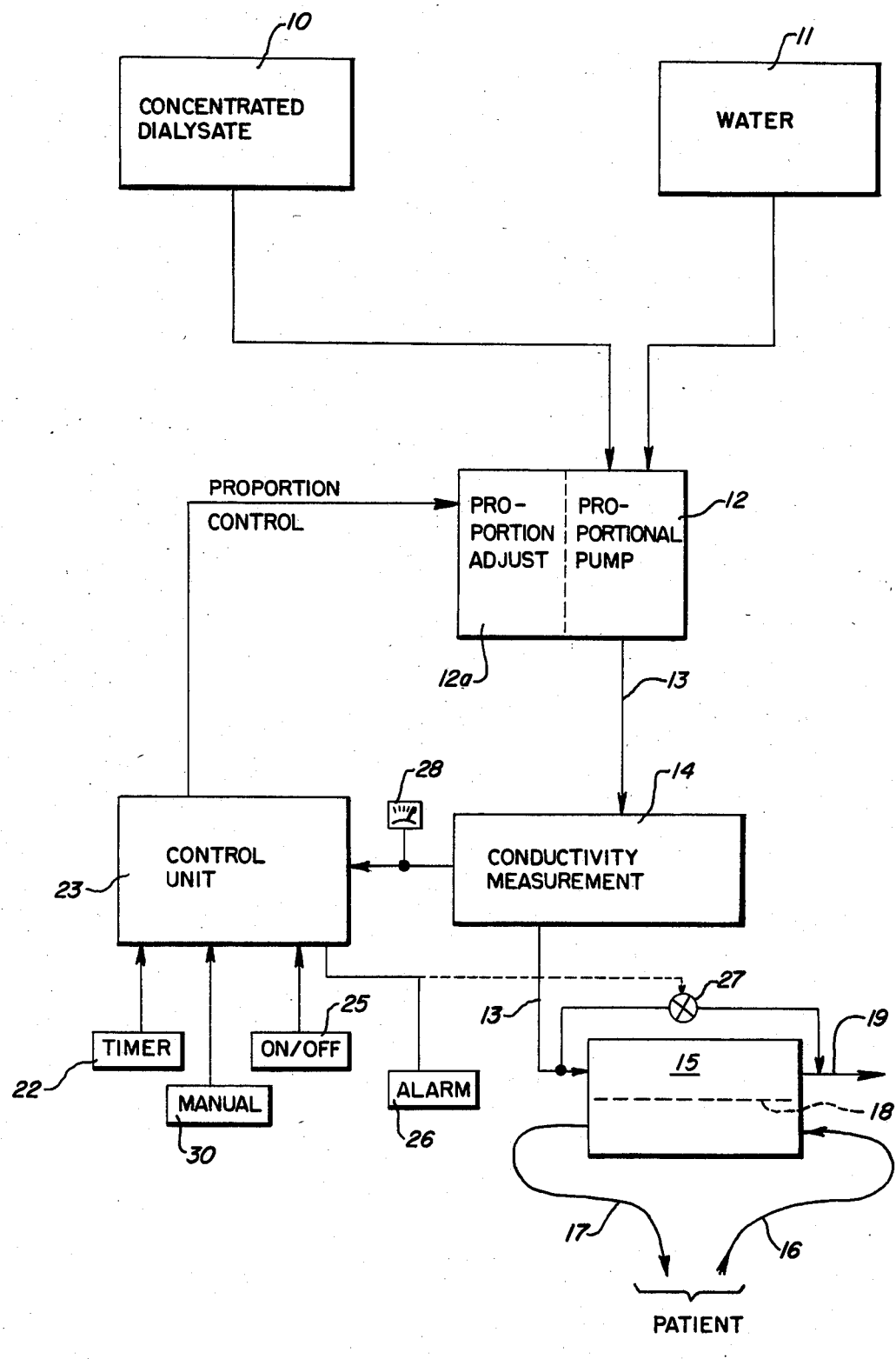
FIG. 1 is a block diagram of a dialysis system illustrating the invention.
Figure 2:
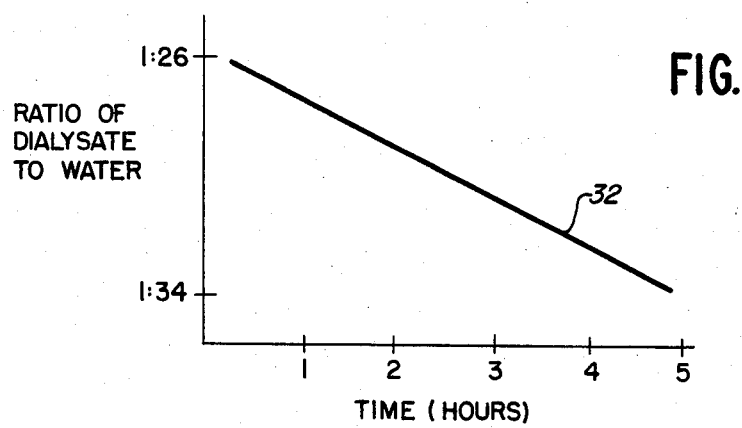
FIG. 2 is a plot of the ratio of dialysis solution concentrate to water as a function of time, illustrating the invention.
Figure 3:
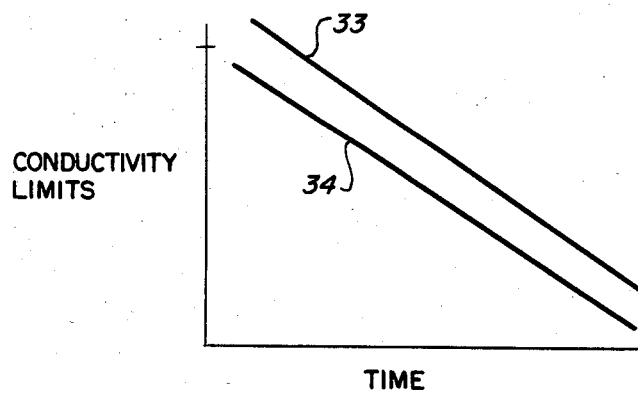
FIG. 3 is a plot of dialysis solution conductivity limits as a function of time, illustrating another aspect of the invention.

Turning now to FIGS. 1, 2 and 3 of the drawings, the method and an apparatus for performing it will be described. A source of concentrated dialysis solution 10 and a source of water 11 are connected with a controllable proportional pump 12, which may be a Drake-Willock pump based on the Willock patents identified above, having a proportion adjust mechanism 12a. This pump mixes the dialysis solution concentrate and water in desired proportions and the resulting dilute dialysis solution is connected by a line 13 through a conductivity measurement apparatus 14 with the dialyzer 15. Blood from the patient is connected with the dialyzer through line 16 and is returned to the patient through line 17. The dashed line 18 represents the semipermeable membrane of the dialyzer. The outflux of dialysate from the dialyzer, carrying wastes received from the blood, is directed to a drain through line 19.

In accordance with the invention, the proportional pump 12 is adjusted at the start of the dialysis operation for a dialysis solution osmolality approximating or even higher than that of the patient's blood. The ratio of dialysis solution concentrate with water may be the order of 1:26 or 1:28. A timer 22 is connected with a control unit 23 which provides a proportion control signal to the proportion control mechanism 12a of proportional pump 12 to modify the pump operation and gradually reduce the concentration of the dialysis solution as a function of time. A typical dialysis procedure lasts four to six hours. During this time the concentration of the dialysis solution is reduced from the starting point to a concentration having an osmolality approximating that desired according to the patient's condition.

Sometimes a patient cannot tolerate low osmolality dialysis solution and develops one or more symptoms of disequilibrium. A manual ON/OFF control 25 provides a means for the operator to interrupt the linear decrease of dialysis solution concentration and continue the dialysis treatment with a fixed dialysis solution concentration.

The conductivity measurement of the dialysis solution provides an indication of its concentration. This measurement is compared with a reference and if the dialysis solution conductivity differs from the conductivity of the intended dialysis solution concentration by an excessive amount, safeguards are initiated as by actuating an alarm 26, which might be a visual or audible signal, for example, and maintaining the proportion adjust mechanism for a constant concentration. A dialyzer bypass valve 27 may be opened to shunt the dialysis solution mixture to the drain 19. The operator may observe the conductivity of the dialysis solution on conductivity meter 28 and manipulate a manual control 30 to establish the desired mixture ratio. The linear decrease of the concentration of the dialysis solution may be restarted with ON/OFF control 25.

In the preferred practice of the invention, the ratio of concentrated dialysis solution to water is reduced linearly as a function of time, as indicated by curve 32 where the ratio is plotted against time hours. The conductivity safeguard circuits preferably utilize high and low conductivity limits with which the dialysis solution conductivity is compared. These limits are similarly varied linearly as a function of time, see FIG. 3. The curve 33 represents the high conductivity limit while curve 34 represents the low conductivity limit. The vertical spacing of curves 33, 34 represent the permitted range of conductivity within which the system operates.

Figure 4:
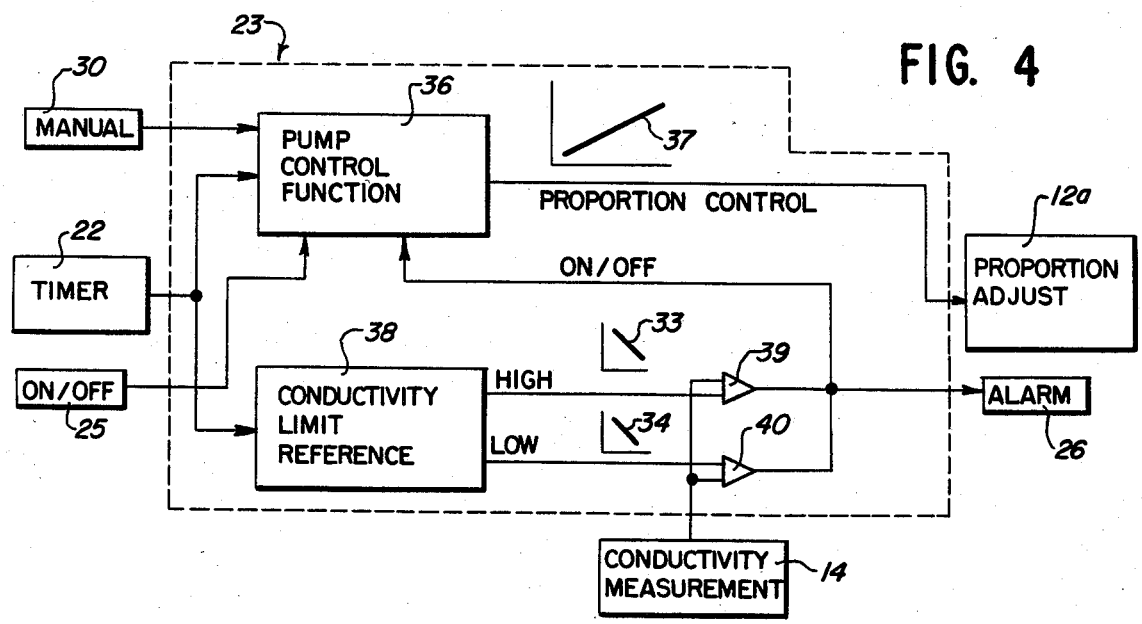
FIG. 4 is a block diagram showing in more detail the control unit of FIG. 1.

FIG. 4 shows in block form an implementation of control unit 23. A signal from timer 22 is connected with a pump control function generator 36 which provides a proportion control signal 37 to proportion adjust mechanism 12a, causing it to reduce the concentration of the dialysis solution linearly with time during the course of the dialysis procedure. The timer also controls a conductivity limit reference generator 38 which has two outputs, one representing the high conductivity limit illustrated graphically at 33 and the other representing the low conductivity limit, 34. The conductivity limit reference signals are connected with comparators 39, 40 to which are also connected a conductivity signal from the conductivity measurement means 14. Comparators 39, 40 provide an on-off control signal to pump control function generator 36 and initiate alarm 26 as shown in FIG. 1. ON/OFF control 25 and manual control 30 are also connected with pump control function generator 36.

The Drake-Willock proportional pump 12 identified above may, if desired, be replaced by a pair of positive displacement rotary pumps one for the concentrated dialysis solution and the other for the heated product water. The speeds of the pumps and thus the relative quantities of the concentrated dialysis solution and water which are mixed are appropriately varied as a function of time by signals from the control unit. Alternatively, a variable speed, positive displacement pump controlled by a proportion control signal may be used to deliver a controlled flow of either dialysis solution concentrate or water to a Drake-Willock pump with fixed ratio. The dialysis solution mixture from the Drake-Willock pump has a decreasing concentration as described above.

The method is not limited to the hemodialysis of blood but may be used in other procedures as a bicarbonate treatment for an acid condition. In this treatment, the concentration of the bicarbonate solution is initiated at a low level and is increased rather than decreased, as a function of time.

I claim:
1. In the hemodialysis of blood by circulation of a dialysis solution in molecular exchange relation with blood to reduce the osmolality of the blood, the improvement comprising:
   initiating the hemodialysis with a dialysis solution having an osmolality of the order of the osmolality of the patient's blood; and
   thereafter varying the osmolality of the dialysis solution as a function of time to achieve the desired osmolality for the patient's condition.
2. The hemodialysis method of claim 1 in which the osmolality of the dialysis solution is reduced continuously with time.
3. The hemodialysis method of claim 1 including the steps:
   establishing upper and lower conductivity limits for the dialysis solution;
   varying both limits in accordance with the variation of the conductivity of the dialysis solution as the osmolality thereof is changed; and
   initiating an alarm in the event the conductivity of the dialysis solution is outside said upper and lower conductivity limits.
4. The hemodialysis method of claim 3 in which the osmolality of the dialysis solution is reduced linearly with time and the upper and lower conductivity limits are reduced linearly with time.
5. In the hemodialysis of blood by circulation of a dialysis solution in molecular exchange relation with blood to reduce the osmolality of the blood, the improvement comprising:
   mixing a concentrated dialysis solution with water for circulation of the dialysis solution mixture through a dialyzer;
   establishing an initial concentration of said dialysis solution mixture having an osmolality of the order of the osmolality of the patient's blood;
   reducing the concentration of the dialysis solution mixture as a function of time;
   measuring the conductivity of the dialysis solution mixture;
   establishing initial upper and lower conductivity limits;
   reducing said upper and lower conductivity limits as a function of time;
   comparing the dialysis solution mixture conductivity with said upper and lower conductivity limits; and
   initiating an alarm if the dialysis solution mixture conductivity is below the lower limit or above the upper limit.
6. The hemodialysis method of claim 5 in which the concentration of the dialysis solution mixture and the upper and lower conductivity limits are reduced continuously as a function of time.

* * * * *